US00PP17742P3

(12) United States Plant Patent
Clark et al.

(10) Patent No.: US PP17,742 P3
(45) Date of Patent: May 15, 2007

(54) PEACH TREE—NAMED 'WHITE COUNTY' CULTIVAR

(50) Latin Name: *Prunus persica*
Varietal Denomination: White County

(75) Inventors: John Reuben Clark, Fayetteville, AR (US); James Norman Moore, Fayetteville, AR (US)

(73) Assignee: University of Arkansas, division of Agriculture, Fayetteville, AR (US)

( * ) Notice: Subject to any disclaimer, the term of this patent is extended or adjusted under 35 U.S.C. 154(b) by 10 days.

(21) Appl. No.: 11/137,630

(22) Filed: May 25, 2005

(65) Prior Publication Data

US 2006/0272063 P1 Nov. 30, 2006

(51) Int. Cl.
*A01H 5/00* (2006.01)

(52) U.S. Cl. ..... Plt./196

(58) Field of Classification Search ..... Plt./194, Plt./196, 195

See application file for complete search history.

*Primary Examiner*—Anne Marie Grunberg
*Assistant Examiner*—S. B. McCormick-Ewoldt

(57) ABSTRACT

Description and specifications of a new and distinct peach variety which originated from a hand pollinated cross of Ark. 392 (non-patented)×Ark. 433N (non-patented) made in 1993 at the University of Arkansas Fruit Substation, Clarksville. This new peach variety can be distinguished by its features of mid-season ripening, high yields of high-quality, attractive, freestone, firm, low-acid, white-flesh fruits, and good plant vigor along with good resistance to bacterial spot disease.

3 Drawing Sheets

Botanical classification: Genus/species: *Prunus persica*. Cultivar: 'White County'.

SUMMARY OF THE INVENTION

The new and distinct variety of peach originated from a hand-pollinated cross of Ark. 392 (non-patented)×Ark. 433N (non-patented) made in 1993 at the University of Arkansas Fruit Substation, Clarksville. The female parent plant used in this hybridization (Ark. 392) is a very firm-fruited, freestone, melting flesh white peach selection not publicly released nor available in commerce and the male parent (Ark. 433N) is a melting flesh, freestone, yellow nectarine selection not publicly released and is unavailable in commerce. Both the parents and the instant variety are the genus and species *Prunus persica*.

The seeds resulting from this controlled hybridization were germinated in a greenhouse in the late winter 1993/early spring of 1994 and planted in a field on the University of Arkansas Fruit Substation, Clarksville, Ark. The seedlings fruited during the summer of 1997 and one, designated Arkansas 678, was selected for its very firm white flesh, mid-reason ripening, large fruits, attractive fruit appearance, excellent fruit quality with low-acid flavor, and resistance to bacterial spot. During 1997, the original plant selection was propagated asexually, at the above-noted location, by budding onto standard peach rootstock variety 'Lovell' (non-patented) and a test plot of two plants was established. Subsequently, larger test plantings have been established with asexually multiplied plants at two additional locations in Arkansas (Clarksville and Hope, Ark.)

The new variety has been asexually multiplied several times since 1997 at this location by budding onto 'Lovell' peach rootstock and no incompatibility with peach rootstocks has occurred following budding. During all asexual multiplication, the characteristics of the original plant have been maintained and no aberrant phenotypes have appeared.

Plants of the new variety are vigorous and productive, and trees are standard in size, well-branched and symmetrical with an upright to semi-spreading growth habit, comparable to other peach trees (*Prunus persica*). Trees express a moderate level of resistance to both foliar and fruit infection of bacterial spot [*Xanthomonas campestris* pv. *pruni* (Smith) Dye] but in some years do not show complete immunity to this disease. The new variety consistently is more resistant to bacterial spot than is the standard white peach variety 'Carolina Belle' (not patented). The new variety blooms in the spring on approximately the same date as'Carolina Belle' and 'Stark® Summer Pearl™' (not patented). No winter cold injury has been observed on wood or buds of the new variety in Arkansas tests where minimum temperatures have reached −13° C. during evaluation. Chilling requirement to break dormancy is estimated to be 750 hours below 7° C.

Fruit of the new variety ripens mid-season, averaging 1 day before 'Carolina Belle' and 12 days before 'Stark® Summer Pearl™' reference white peach varieties. Average first ripening date is July 14 in west-central Arkansas (Clarksville). Fruit of the new variety has not been observed to have split pits, a serious fruit disorder of some peach varieties. Fruit yields have been good and have averaged higher than those of the comparison peach varieties 'Carolina Belle', and 'Stark® Summer Pearl™' in test comparisons.

The fruit is round to slightly oval in shape, without a prominent tip and a slight suture bulge. Fruits are attractive with an average 83% bright red blush, and 17% white or cream skin background color. Fruit finish is good with no blemishes. The fruit skin has average pubescence like other peaches. The flesh of the fruit is white in color and has slight red pigment in the flesh, mostly around the stone or pit. Flesh is melting but very firm until fully mature when it softens. The fruit is a freestone, in that the flesh does not adhere to the pit. Fruit size is large averaging 258 g.

The fresh fruit rates excellent in flavor, and was rated highly in evaluations. Fruits average 13.9% soluble solids. The flavor is sweet and low-acid, with a distinct white peach aroma.

The most distinctive features of the new variety are its early mid-season ripening, high yields of high-quality, attractive, freestone, firm, low-acid, white-flesh fruits, and good plant vigor along with good resistance to bacterial spot disease.

The new variety has been named the 'White County' cultivar.

BRIEF DESCRIPTION OF THE PHOTOGRAPHS

The accompanying photographs show typical specimens of the fruit (FIGS. 1 and 2) and leaf (FIG. 3) of the new variety in color as nearly true as it is reasonably possible to make in a color illustration of this character.

DETAILED BOTANICAL DESCRIPTION OF THE NEW VARIETY

The following is a detailed description of the botanical and pomological characteristics of the subject peach. Color data are presented in Royal Horticultural Society Colour Chart designations.

Where dimensions, sizes, colors and other characteristics are given, it is to be understood that such characteristics are approximations of averages set forth as accurately as practical.

The descriptions reported herein are from specimens grown at Clarksville, Ark. and are from trees grown in trickle (drip) irrigated orchards growing on a Linker fine sandy loam soil. The data were collected from six-year old trees of the instant variety except yield data that were taken on five-year-old trees in a replicated test planting.

Plant:

*Size.*—Mature trees (5 years of age and older) average 3.4 m to 3.7 m in height and 4.8 to 5.9 m in spread or width, and a semi-upright growth habit, as grown on 'Lovell' rootstock using an open-center training system commonly used on peaches. Tree size is comparable to that of the 'Carolina Belle' and 'Stark' 'Summer Pearl'™ varieties.

*Growth.*—Vigorous, symmetrical form, good canopy development. Vigor comparable to that of the 'Carolina Belle' and 'Stark Summer Pearl'™ varieties.

*Productivity.*—Very productive and consistent from year to year. Yield measured 23.4 kg/tree on five-year old trees and exceeding that of 'Carolina Belle' with 20.8 kg/tree and 11.0 kg/tree for 'Summer Pearl'™ in a test planting of identical age and growing conditions.

*Cold hardiness.*—Wood and dormant buds hardy to −13° C.

*Disease resistance.*—Leaves and fruit resistant but not immune to bacterial spot under growing conditions where bacterial spot infection is often very severe on susceptible genotypes. No bactericides were used in the development or evaluation of the instant cultivar. Evidence of bacterial spot infection was less than that of 'Carolina Belle' in all years of evaluation. A commercial fungicide program was utilized in orchards used in the development and evaluation of the instant variety, thus no resistance to brown rot or scab, the other common diseases at Clarksville, Ark., was determined.

*Insect resistance.*—Insecticides were applied to orchards used in the development of the instant variety to control the common insects at the location including oriental fruit moth, plum curculio, stinkbug, tarnished plant bug, lesser peach tree borer, and greater peach tree borer. Therefore no insect resistance was determined in the testing of the instant variety.

Foliage/shoots/branches:

*Shoots.*—Smooth. Current growing-season mature shoot length 43.2 cm; diameter base 0.5 cm, midpoint 0.4 cm, terminal 0.2 cm (measured in July of the growing season). Dormant-season shoot (branch): length 44.2 cm; diameter at base 0.5 cm; diameter at midpoint 0.4 cm; diameter at terminal 0.3 cm. Dormant-season shoot color Greyed-Purple Group (183A); Dormant-season shoot texture smooth.

*Leaves.*—Simple, alternate, glabrous, lanceolate, petiolate, deciduous. Venation pinnate; base acute; terminal or apex acuminate; margin serrated. Mature leaf size: length 16.4 cm; width midpoint 3.8 cm. Leaf serrations; 4.5 /cm. Mature leaf color: abaxial — Yellow-Green Group (147B); adaxial — Yellow-Green Group (137A); and anthocyanin not present on abaxial or adaxial side of mature leaves on midrib or other location. Young leaf color: abaxial — Yellow-Green Group (146B); adaxial — Yellow Green Group (146A); anthocyanin not present on abaxial or adaxial side of young leaves on midrib or other location. Petiole length — mature leaf: 1.1 cm. Leaf glands: reniform, 4 per leaf usually, located at base of leaf blade at top of petiole. Leaf glands are 0.10 cm in width and 0.16 cm in length.

*Buds.*—Number of leaf buds per 15 cm: 6, evenly distributed along the shoot. Number of flower buds per 0–15 cm from terminal: 9. Mature shoot internode length: base 1.7 cm, midpoint 2.0 cm, terminal 1.3 cm.

Bark (of mature trunk of tree):

*Color.*—Greyed-Green Group (197C).

*Texture.*—Rough.

Trunk:

*Diameter.*—15.3 cm (at 25 cm above ground level).

Flower buds: Dormant flower bud length 0.4 cm and diameter 0.2 cm and color Greyed-Orange Group (166A); dormant buds swell and expand in late winter and increase in size during this expansion to fully open flowers. Color changes to that of the adaxial petal color Red-Purple Group (65C).

Flowers: Bloom occurs prior to vegetative bud break; solitary to occasional double individual flowers at a single node; perfect; self-fertile.

*Date of bloom.*—First, Julian 80 (March 20); Full, Julian 86 (March 26).

*Size.*—Diameter fully open 4.0 cm.

*Type.*—Showy.

*Color.*—Adaxial: Red Purple Group (65B); abaxial: Red-Purple Group (65D).

*Petals per flower.*—5.

*Length of pistil.*—2.0 cm.

*Stamens.*—Average 49.8/flower with pollen present, fertile and abundant.

*Ovary.*—Pubescent.

Fruit:

*Size.*—Large, avg. 257.7 g; diameter stem end 7.0 cm, equator 7.6 cm, blossom end 6.6 cm; length base to apex 7.4 cm.

*Shape.*—Round, symmetrical, and occasionally some fruits slightly oblate. Fruits are without pronounced tip but slight suture bulge.

*Skin.*—Pubescent (fuzzy), attractive; ground color Yellow-White Group (158A), with red blush (Red Group 53B), over 83% of surface on average.

*Flesh.*—Yellow-White Group (158A); freestone; melting texture; good firmness. Firmness when measured by a fruit pressure tester (using a McCormick model FT327 fruit pressure tester, 11 mm diameter probe, McCormick Fruit Tree Co., Yakima, Wash.) on unpeeled fruit had average firmness value of 4.4 kg. Excellent eating quality; flavor sweet, subacid, with pronounced white peach flavor and aroma.

*Pedicel length.*—0.8 cm.

*Pedicel diameter.*—0.4 cm.

*Pedicel color.*—Yellow-Green Group (144B).

*Ripe date.*—July 14 (Julian 196) in west-central Arkansas. Ripening of individual fruit is uniform.

*Tendency of pit to split.*—No split pits most years.

*Soluble solids.*—13.9%.

*Fruit juice pH.*—4.34.

Pit/stone:

*Size.*—Length 4.0 cm; diameter (midpoint) 1.94 cm.

*Shape.*—Slightly oblong with deep furrowing and pitting.

*Color.*—Greyed-Red Group (178A).

Kernel:

*Size.*—Length 2.0 cm; diameter varies with dryness of the kernel but is up to 0.4 cm.

*Shape.*—Almond.

*Color.*—Greyed-Orange Group (164B).

Uses: Fresh consumption, not evaluated for drying or other uses.

The variety: The most distinctive features of the new variety are its mid-season ripening, high yields of high-quality, attractive, freestone, firm, low-acid, white-flesh fruits, and good plant vigor along with good resistance to bacterial spot disease.

We claim:

1. A new and distinct variety of peach tree (*Prunus persica* cultivar 'White County') as herein described and illustrated, characterized by its mid-season ripening, high yields of high-quality, attractive, freestone, firm, low-acid, white-flesh fruits, and good plant vigor along with good resistance to bacterial spot disease.

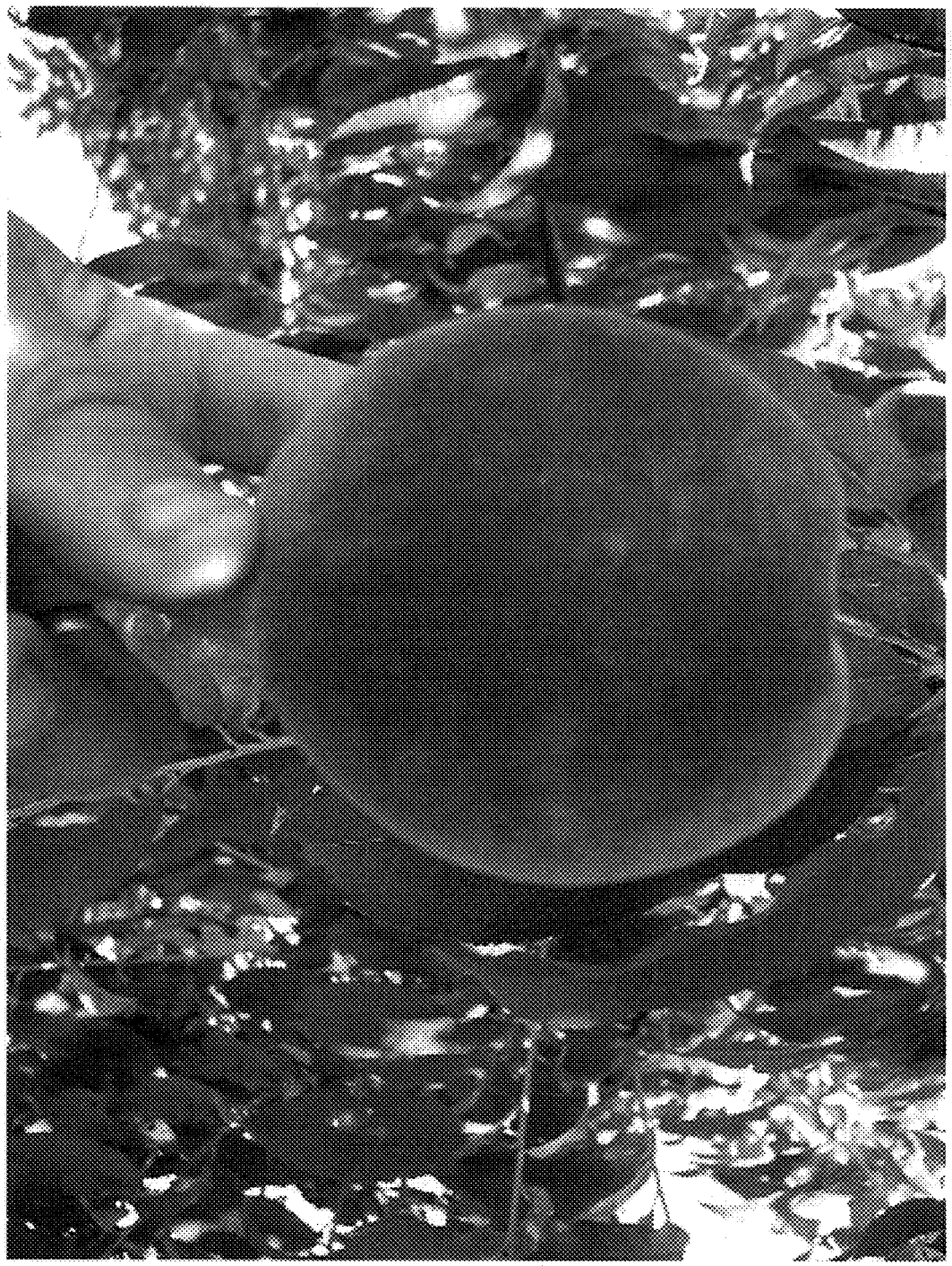

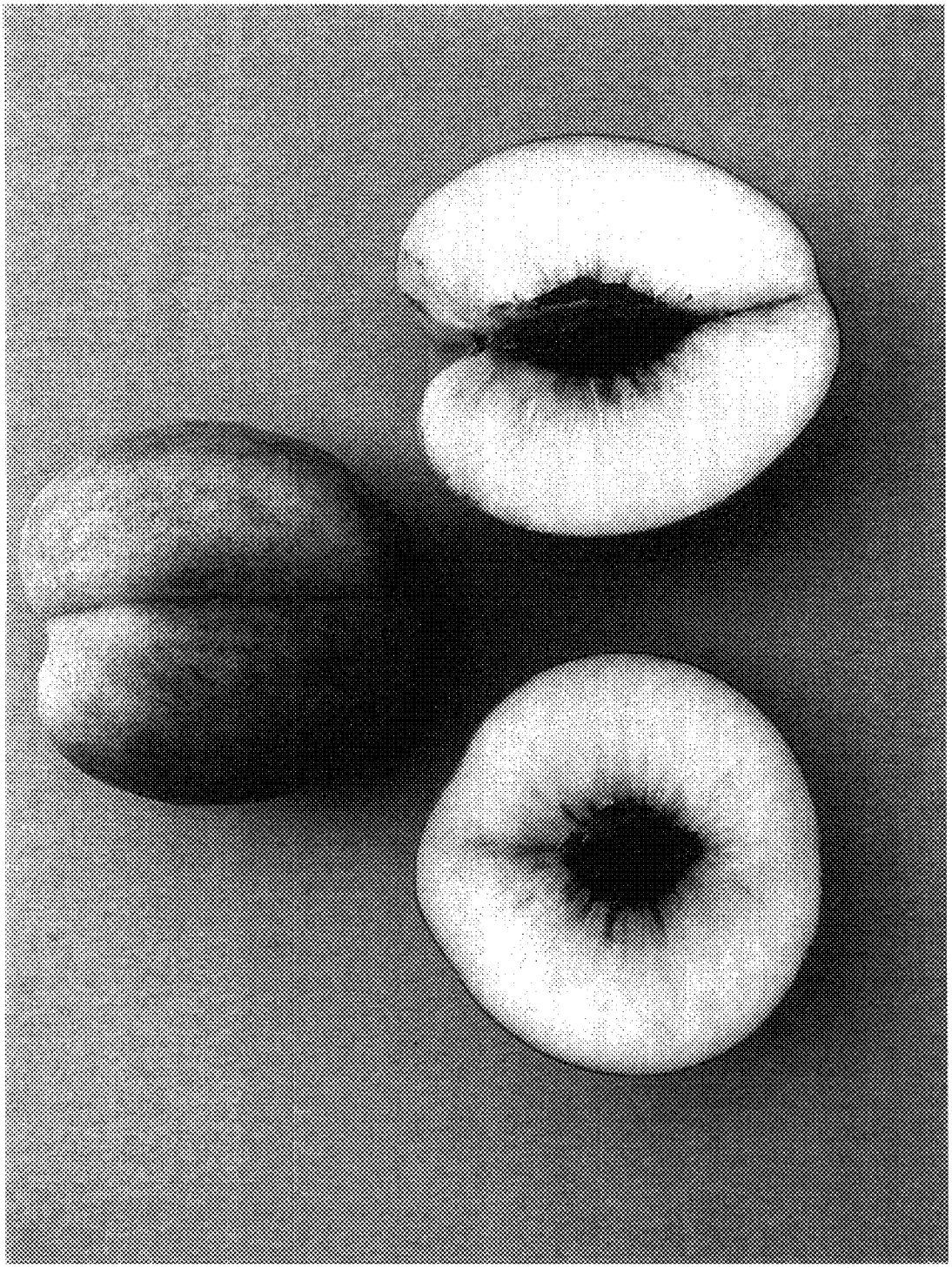

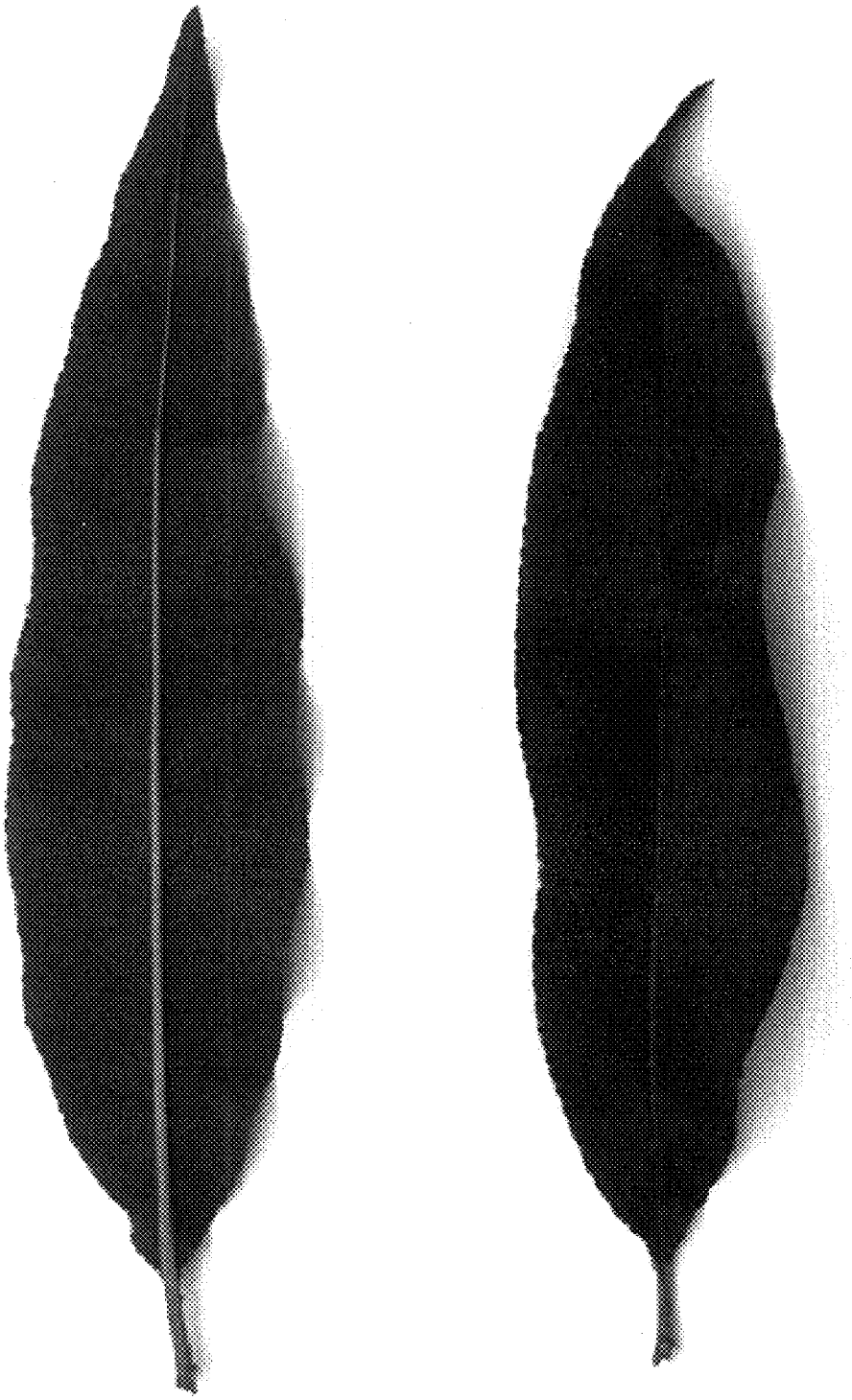

* * * * *